(12) United States Patent
Zuk et al.

(10) Patent No.: US 7,445,887 B2
(45) Date of Patent: Nov. 4, 2008

(54) ENZYME ACTIVITY MEASUREMENTS USING BIO-LAYER INTERFEROMETRY

(75) Inventors: Robert Zuk, Atherton, CA (US); Sae Choo, San Jose, CA (US); Weilei Ma, Palo Alto, CA (US); Krista Witte, Hayward, CA (US)

(73) Assignee: ForteBio, Inc., Menlo Park, CA (US)

( * ) Notice: Subject to any disclaimer, the term of this patent is extended or adjusted under 35 U.S.C. 154(b) by 189 days.

(21) Appl. No.: 11/326,689

(22) Filed: Jan. 6, 2006

(65) Prior Publication Data

US 2006/0154320 A1 Jul. 13, 2006

Related U.S. Application Data

(60) Provisional application No. 60/645,153, filed on Jan. 19, 2005, provisional application No. 60/642,454, filed on Jan. 7, 2005.

(51) Int. Cl.
C12Q 1/00 (2006.01)
(52) U.S. Cl. .......................... 435/4; 356/901
(58) Field of Classification Search .............. 435/4
See application file for complete search history.

(56) References Cited

U.S. PATENT DOCUMENTS

| | | | |
|---|---|---|---|
| 4,830,451 A | 5/1989 | Stone | |
| 5,301,001 A | 4/1994 | Murphy et al. | |
| 5,359,405 A | 10/1994 | Andrews | |
| 5,422,970 A | 6/1995 | Miller et al. | |
| 5,425,039 A | 6/1995 | Hsu et al. | |
| 5,452,087 A | 9/1995 | Taylor et al. | |
| 5,528,367 A | 6/1996 | Putnam et al. | |
| 5,594,819 A | 1/1997 | Narendran et al. | |
| 5,606,170 A | 2/1997 | Saaski et al. | |
| 5,629,214 A | 5/1997 | Crosby | |
| 5,631,171 A | 5/1997 | Sandstrom et al. | |
| 5,647,038 A | 7/1997 | Minden et al. | |
| 5,682,237 A | 10/1997 | Belk | |
| 5,701,193 A | 12/1997 | Vogel et al. | |
| 5,732,169 A | 3/1998 | Riant et al. | |
| 5,804,453 A | 9/1998 | Chen | |
| 5,869,835 A | 2/1999 | Udd | |
| H1813 H | 11/1999 | Kersey | |
| 5,982,959 A | 11/1999 | Hopenfeld | |
| 6,055,080 A | 4/2000 | Furstenau et al. | |
| 6,078,706 A | 6/2000 | Nau et al. | |
| 6,139,797 A | 10/2000 | Suzuki et al. | |
| 6,241,397 B1 | 6/2001 | Bao et al. | |
| 6,244,214 B1 | 6/2001 | Hebrank | |
| 6,248,539 B1 | 6/2001 | Ghadiri et al. | |
| 6,254,830 B1 | 7/2001 | Pivarnik et al. | |
| 6,275,628 B1 | 8/2001 | Jones et al. | |
| 6,277,651 B1 | 8/2001 | Groger et al. | |
| 6,281,976 B1 | 8/2001 | Taylor et al. | |
| 6,445,838 B1 | 9/2002 | Caracci et al. | |
| 6,496,618 B1 | 12/2002 | Fernando et al. | |
| 6,539,136 B1 | 3/2003 | Dianov et al. | |
| 6,571,639 B1 | 6/2003 | May et al. | |
| 6,590,665 B2 | 7/2003 | Painchaud et al. | |
| 6,611,334 B1 | 8/2003 | Fernando et al. | |
| 6,661,520 B1 | 12/2003 | Lin et al. | |
| 6,671,055 B1 | 12/2003 | Wavering et al. | |
| 6,687,011 B1 | 2/2004 | Lee et al. | |
| 6,720,177 B2 | 4/2004 | Ghadiri et al. | |
| 6,744,939 B2 | 6/2004 | Lampert et al. | |
| 6,870,624 B2 | 3/2005 | Hobbs et al. | |
| 6,870,630 B2* | 3/2005 | Budach et al. | 356/521 |
| 7,158,225 B2 | 1/2007 | Tedesco et al. | |
| 2001/0048072 A1 | 12/2001 | Painchaud et al. | |
| 2002/0127565 A1* | 9/2002 | Cunningham et al. | 435/6 |
| 2003/0112443 A1 | 6/2003 | Hjelme et al. | |
| 2003/0215791 A1* | 11/2003 | Garini et al. | 435/5 |
| 2004/0022475 A1 | 2/2004 | Pennington | |
| 2004/0151626 A1* | 8/2004 | Cunningham et al. | 422/58 |
| 2004/0186359 A1 | 9/2004 | Beaudoin et al. | |
| 2005/0254062 A1* | 11/2005 | Tan et al. | 356/480 |
| 2006/0050358 A1 | 3/2006 | Bigman | |
| 2007/0070356 A1* | 3/2007 | Tan et al. | 356/477 |

FOREIGN PATENT DOCUMENTS

WO WO 2005/047854 A2 * 5/2005

OTHER PUBLICATIONS

Brecht A. et al. Recent Developments in Optical Transducers for Chemical or Biochemical Applications. Sensors and Actuators B 38-39, 1-7, 1997.*

Lim, S. et al., Application of an Interferometric Biosensor Chip to Biomonitoring an Endocrine Disruptor. Biotechnology and Bioprocess Engineering. 2004, vol. 9, No. 2, pp. 118-126.

(Continued)

*Primary Examiner*—Ralph Gitomer
(74) *Attorney, Agent, or Firm*—Fenwick & West LLP

(57) ABSTRACT

Disclosed are enzyme assays using biolayer interferometry. Assays may be carried out using immobilized substrate or with a substrate capture format. In certain embodiments, the assays are carried out using unlabeled substrates. The methods are broadly applicable to enzyme assay measurements, can be carried out in vivo or in vitro, and are easily multiplexed.

18 Claims, 13 Drawing Sheets

OTHER PUBLICATIONS

PCT International Search Report and Written Opinion, Aug. 4, 2006, PCT/US06/00700.
Reagent Reservoirs with Control Wells, V&P Scientific, Inc., 2006, [online] [Retrieved on Sep. 6, 2006] Retrieved from the Internet <URL:http://www.vp-scientific.com/reagent_reservoirs_with_control_.htm>.
Boiarski, A. et al., "Integrated-Optic Biosensor", SPIE, Fiber Optic Sensors in Medical Diagnostics, vol. 1886, 1993, pp. 15-26.
Brecht, A. et al., "Direct Monitoring of Antigen-Antibody Interactions by Spectral Interferometry", Sensors and Actuators, vol. B5, 1992, pp. 96-100.
Brecht, A. et al., "Interferometric Immunoassay in an FIA-System: a Sensitive and Rapid Approach in Label-free Immunosensing", Biosensors & Bioelectronics, vol. 8, 1993, pp. 387-392.
Brecht, A. et al., "Theoretical and Experimental Detectivity of the RIFS—transducer in Affinity-sensing", Biosensors 94, The Third World Congress on Biosensors: Abstracts, Oral Session, Jun. 2, 1994, p. 68.
Brecht, A. et al., "Recent Developments in Optical Transducers for Chemical or Biochemical Applications," Sensors and Actuators B, Jan. 1997, pp. 1-7, vol. 3-39, Elsevier Science S.A., Lausanne, CH.
Christensen, D. et al., "Analysis of Excitation and Collection Geometries for Plannar Waveguide Immunosensors," SPIE vol. 1886, Fiber Optic Sensors in Medical Diagnostics, 1993, pp. 2-8.
Davies, R. et al., "An Optical Biosensor System for Molecular Interaction Studies", American Biotechnology Laboratory, Jul. 1993.
Elster, J. L. et al., "Optical Fiber Extrinsic Fabry-Perot Interferometric (EFPI)-Based Biosensors," Proceedings of the SPIE, 2000, pp. 105-112, vol. 3911.
Cao, L. et al., "Detection of Yersinia Pestis Fraction 1 Antigen With a Fiber Optic Biosensor", Journal of Clinical Microbiology, vol. 33, No. 2, Feb. 1994, pp. 336-341.
Gauglitz, G. et al., "Observation of Spectral Interferences for the Determination of Volume and Surface Effects of Thin Films", Analytical Biochemistry, vol. 341, 1991, pp. 279-283.
Fabricius, N. et al., "A Gas Sensor Based on an Integrated Optical Mach-Zehnder Interferometer", Sensors and Actyators, vol. B7, 1992, pp. 672-676.
Hogg, D. et al., "Development of a Fiber Fabry-Perot Strain Gauge", SPIE vol. 1588, Fiber Optic Smart Structures and Skins IV, 1991, pp. 300-307.
Jorgenson, R. et al. "A Novel Surface Plasmon Resonance Based Fiber Optic Sensor Applied to Biochemical Sensing", SPIE, vol. 1886, 1993, pp. 35-48.
Kimoshita, Y. et al., "Sensing of Herbicide Residues Using Surface Plasmon Resonance Technique", The Third World Congress on Biosensors: Abstracts, 1994, p. 257.
Lin, C-J., et al., "A Novel in Vitro and in Situ Immunoassay Biosensor Based on Fiber Optic Fabry-Perot Interferometry," Proceedings of the SPIE, The International Society for Optical Engineering, 2004, pp. 304-307, vol. 5502, No. 1.
Lukosz, W., et al., "Output grating Coulers on Planar Optical Waveguides as Direct Immunosensors", Biosensors & Bioelectronics, vol. 6, 1991, pp. 227-232.
Lundstrom, I., et al. "Immunosensors Based on Surface Plasmon Resonance", The Third World Congress on Biosensors: Abstracts, 1991, p. 91.
Ogert et al., "Detection of Clostridium Botulinum Toxin A Using a Fiber Optic-Based Biosensor", Analytical Biochemistry, vol. 205, 1992, pp. 306-312.
Rudraraju, S. et al., "Acoustic Wave Propagation in Composite Materials: an Experimental Study", SPIE, vol. 2191, Jul. 1994, pp. 487,493.
Schneider, I. et al., "Herbicide Detection Using Reaction, Centers Integrated Into Liposomes Binding to Grating Couplers", The Third World Congress on Biosensors: Abstracts, 1994, p. 271.
Tiefenthaler, K., "Grating Couplers as Label-free Biochemical Waveguide Sensors", Biosensors & Bioelectronics, vol. 8, No. 7-8, pp. xxxv-xxxvii, no date given.
Weber, A. et al., "Fiber-optic Fluorimetry in Biosensors: Comparison Between Evanescent Wave Generation and Distal-face Generation of Fluorescent Light", Biosensors & Bioelectronics, vol. 7, 1992, pp. 193-197.
Yang Y. et al., "Direct Monitoring of Antigen-Antibody Interactions by Optical Fiber Bioprobe," Proceedings of the SPIE, Jun. 8, 2003, pp. 431-436, vol. 5254, No. 1.
Yang, Y. et al., "Study of Optical Fiber Biosensor Based on White-Light Interferometry," Journal of Xi'An Jiaotong University, Sep. 2003, pp. 914-916, 988, vol. 37, No. 9, Xian, CN.
Office Action, Chinese Application No. 200480031823.5, Jul. 20, 2007, 16 pages.
European Supplementary Search Report, EP 04800761, Mar. 19, 2007, 4 pages.
European Examination Report, EP 04800761.1, Nov. 23, 2007, 5 pages.
PCT International Search Report and Written Opinion, PCT/US06/22964, Jun. 1, 2007, 9 pages.
PCT International Search Report and Written Opinion; PCT/US04/36830, Sep. 6, 2005, 9 pages.

* cited by examiner

Fig. 1 Minimum Molecular Size Detection

Fig. 2 Minimum Molecular Size Detection

Fig. 4 Protease Assay (Casein / Subtilisin Pair)

Fig. 5 The Effect of Protease Inhibitor
(Subtilisin / PMSF Pair)

The Effect of Protease Inhibitor
(Subtilisin / PMSF Pair)

Fig. 7 Substrate Capture Format

Peptide substrate: biotin substitution positions

A.) Protease has multiple cleavage sites, Biotin substitution does not have to be site specific for significant molecular size change B.) Protease has single cleavage site, Biotin substitution is adjacent to cleavage site to produce smallest fragment Fig. 9 Detection of Nucleotide Transferase Activity Fig. 10  Nucleotide Transferase Activity with Hapten Incorporation Fig. 11 Phosphotransferase Activity: Antibody to Phosphorylated Substrate

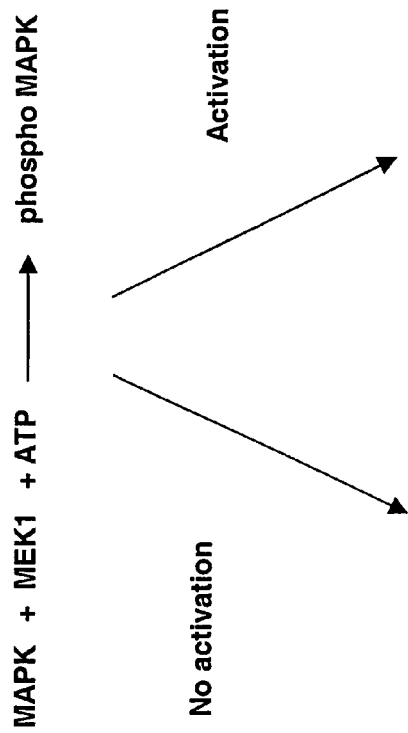
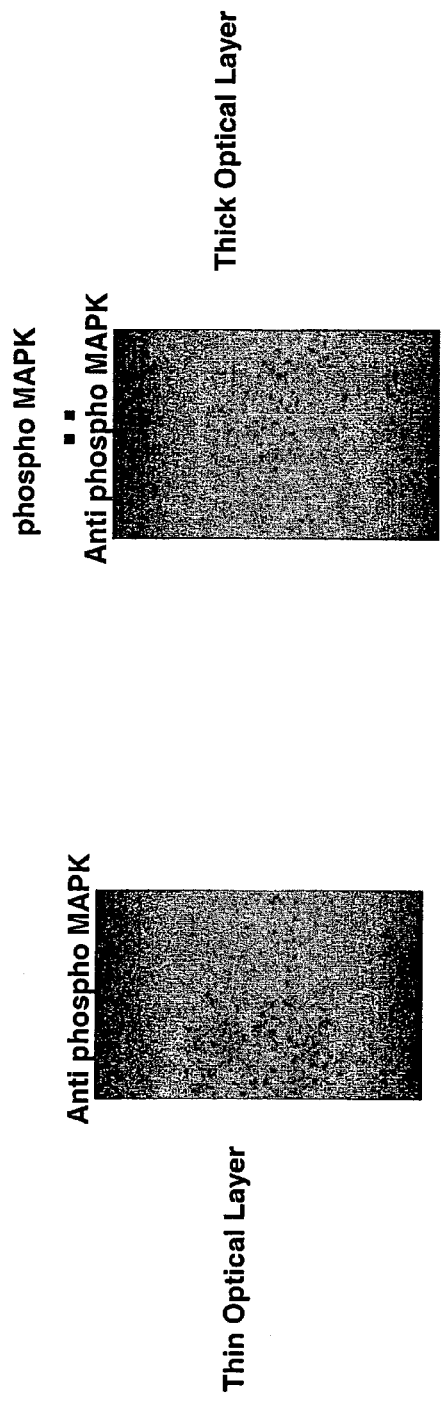
Fig. 13 Activation of Mitogen Activated Protein Kinase (MAPK)

ENZYME ACTIVITY MEASUREMENTS USING BIO-LAYER INTERFEROMETRY

CROSS REFERENCE TO RELATED APPLICATIONS

The present application claims the benefit of U.S. Provisional Application Ser. No. 60/645,153, filed Jan. 19, 2005 and U.S. Provisional Application Ser. No. 60/642,454, filed Jan. 7, 2005, both of which are incorporated herein by reference in their entirety for all purposes.

STATEMENT REGARDING FEDERALLY SPONSORED RESEARCH OR DEVELOPMENT

Not applicable.

BACKGROUND OF THE INVENTION

1. Field of the Invention

The invention relates to interferometry-based methods and compositions useful for measuring enzyme activity.

2. Description of the Related Art

Enzymes represent a broad class of proteins that catalyze biochemical reactions and have many therapeutic and industrial applications. Often in the course of development and manufacture of enzyme products it is necessary to measure the activity of the enzyme. A simple enzyme activity method, preferably label free thereby avoiding perturbation of the enzyme/substrate interaction, would find wide application. In the development and manufacture of enzyme or enzyme inhibitor based products for therapeutic or industrial applications, it is critical to monitor the activity of the enzyme throughout the process. Enzyme assays typically require labeling the substrate in such a way that the enzyme acting on the substrate produces a detectable change in signal. Labeled enzyme substrates are often not commercially available, in which case their synthesis can be complex. For companies developing a multitude of enzyme products, the implementation of activity methods that are simple and easy to perform in research & development and manufacturing environments becomes a major task. The need for labeled substrates adds to the time, expense and inconvenience of enzyme activity measurements. Specific activity measurements also require quantifying the amount of enzyme present in a sample. Quantitation, as by, e.g., enzyme-linked immunosorbant (ELISA)-based assays are also adds to the time and expense of specific activity measurements and requires additional sample. The present invention addresses these and other shortcomings of the prior art by providing simple, fiber based, real-time enzyme activity assays, capable of providing specific activity measurements, suitable for low-volume samples, that are highly multiplexable and in some embodiments can be carried out using unlabeled substrates.

SUMMARY OF THE INVENTION

The present invention is defined by the following claims, and nothing in this section should be taken as a limitation on those claims. Disclosed herein are assemblies, kits, and methods for assaying enzyme activity using fiber-based interferometry. In one embodiment, the assay comprises providing an optical element coupled to a light source via an optical fiber and the element includes proximal and distal reflecting surfaces separated by at least 50 nm. A layer of enzyme substrate molecules is positioned so that interference between beams reflected from the proximal and distal reflecting surfaces varies as an enzyme reacts with the substrate. The reflected beams are coupled into the optical fiber. The element is exposed to an enzyme and a change is detected in the interference between the reflected beams. The detected change is indicative of enzyme activity.

In still another embodiment, a layer of analyte binding molecules substituted in the optical element for the layer of enzyme substrate molecules. Interference between beams reflected from the proximal and distal reflecting surfaces varies as an enzyme reacts with the substrate and the acted-upon substrate or portion thereof binds to the analyte binding molecules. In preferred embodiments, the analyte binding molecules comprise an antibody, an antibody fragment, a single chain Fv molecule ("scFv"), an avidin, a streptavidin, or a biotin.

In another embodiment, a semi-permeable membrane is placed between the optical element and the assay solution. In another embodiment, the substrate is coupled to a support such as a microtitre well or a bead.

In yet another embodiment, a similar, second element is provided that includes a layer of molecules that specifically binds to the enzyme. The second element is exposed to an enzyme (either at the same time or at a different time as the first element is exposed) and a change is detected in the interference between the reflected beams. The change is indicative of enzyme concentration or amount. This is useful for carrying out specific activity measurements. In preferred embodiments, the enzyme-binding molecules comprise an anti-enzyme antibody, an antibody fragment or an scFv molecule.

BRIEF DESCRIPTION OF THE SEVERAL VIEWS OF THE DRAWING

These and other features, aspects, and advantages of the present invention will become better understood with regard to the following description, and accompanying drawings, where:

FIG. 7A illustrates substrate having multiple protease cleavage sites; FIG. 7B illustrates substrate having single (or few) cleavage sites;

FIG. 13 is a schematic illustrating method to detect activation of mitogen activated protein kinase (MAPK).

DETAILED DESCRIPTION OF THE INVENTION

Advantages and Utility

Figure 1:
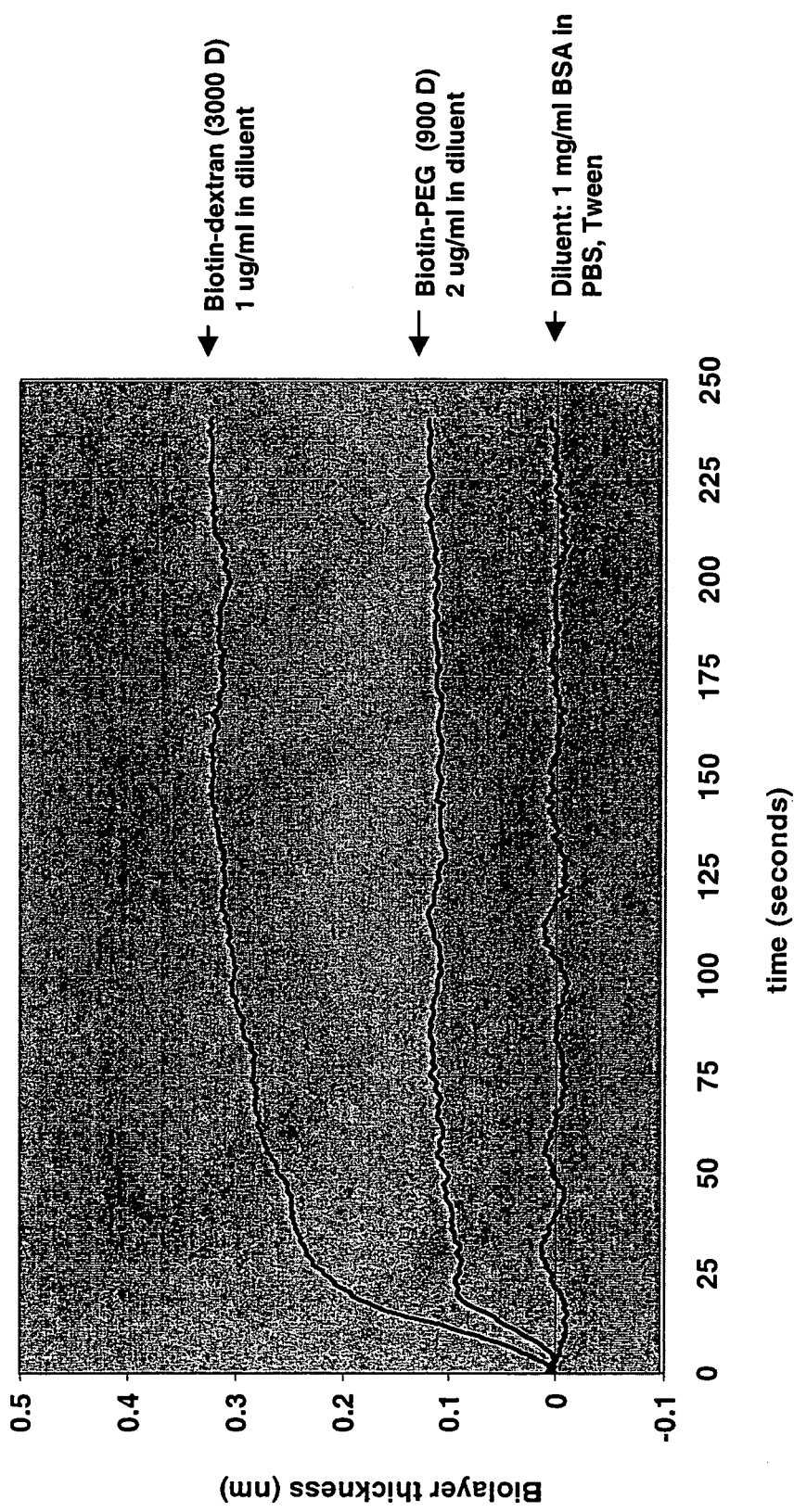
FIG. 1 is a graph illustrating minimum molecular size detection.

Briefly, and as described in more detail below, described herein are assemblies, kits and methods for assaying enzyme activity using fiber-based interferometry.

Several features of the current approach should be noted. Measurements can be carried out using extremely small sample volumes (e.g., nL). Measurements can be carried out in vivo or in vitro. In some embodiments, measurements can be carried out on unlabeled substrates while in other embodiments, substrates include a moiety to allow capture by the assembly. In preferred embodiments, the moiety is one member of a binding pair such as, e.g., avidin, streptavidin, biotin, a hapten, an antibody, antibody fragment, an scFv, or a lectin, and the optical element comprises the complementary member of the pair. In these embodiments, the same type of optical element (i.e., carrying one member of the binding pair) can be used in a wide variety of enzyme assays provided the substrate includes the other member of the pair.

Advantages of this approach are numerous. Because the invention provides for fiber-based interferometry measurements, it is sensitive, capable of being highly multiplexed, and easily adapted for specific activity measurements by including a module for measuring enzyme amount.

The invention is useful for measuring enzyme activity in any context for which such activity measurements are useful including, e.g., for discovery, modification, optimization, production, etc. of enzymes or enzyme inhibitors. The invention may be practiced using any type of enzyme such as, e.g., hydrolases, glycosylases, esterases, and transferases, or inhibitors of such enzymes.

Definitions

Terms used in the claims and specification are defined as set forth below unless otherwise specified.

The term "in vivo" refers to processes that occur in a living organism.

Abbreviations used in this application include the following: dsDNA—double-stranded DNA; dNTPs—deoxynucleotide triphosphates; B-ATP—biotinylated-ATP; PEG—polyethylene glycol, PMSF—phenylmethylsulfonyl fluoride.

It must be noted that, as used in the specification and the appended claims, the singular forms "a," "an" and "the" include plural referents unless the context clearly dictates otherwise.

Assemblies of the Invention

Assemblies of the invention include biosensor tips adapted for coupling to a bio-layer interferometer and carrying a layer of substrate or an analyte binding molecule. The analyte binding molecule may be by way of example and not limitation, a member of a binding pair such as, e.g., avidin, streptavidin, biotin, a hapten, an antibody, an antibody fragment, an scFv, or a lectin.

Kits of the Invention

Kits of the invention include a glass fiber adapted for coupling to a bio-layer interferometer, reagents and instructions for derivatizing the glass fiber with a substrate layer or an analyte binding molecular layer, optionally reagents and instructions for optically activating an end of the glass fiber and packaging.

Methods of the Invention

In general, methods of the invention are practiced using assemblies and apparatus, including a bio-layer interferometry (BLI) sensor, such as those described in co-owned U.S. Non-provisional application Ser. No. 10/981,901, filed Nov. 4, 2004, for Hong Tan, et al., entitled "Fiber-Optic Assay Apparatus Based on Phase-Shift Intepferometry," the contents of which are herein incorporated by reference in their entirety.

In brief, the sensor is prepared by optically activating one end of a glass fiber. The activation steps include buffing the fiber surface, coating the surface with $Ta_2O_5$ followed by coating with an $SiO_2$ layer, and cleaning, and immobilization of enzyme substrate or one member of a binding pair by passive adsorption and/or covalent attachment.

Included within the scope of the invention are two broad and general formats for assaying enzyme activity. In the first format, substrate is immobilized on a surface of a bio-layer interferometry (BLI) sensor. In the second format, the BLI sensor includes a surface having a molecule capable of binding substrate. In the second format, a semi-permeable membrane optionally is included between the BLI sensor and the assay solution, or the substrate is bound to a support such as a microtitre well or a bead. These embodiments are particularly useful with hydrolases to prevent or slow binding of full-length substrate to the BLI sensor. In the second format, information about enzyme activity can be derived both from kinetic and steady state components of the interference signal.

A Bio-Layer Interferometry (BLI) sensor is capable of measuring sub nanometer changes in the thickness of its optical layer detection surface. Analysis of biological samples is possible by designing assay formats where biomolecules bind at the sensor surface and change the optical layer thickness. The magnitude of the optical layer thickness change is proportional to the mass or molecular weight of the binding molecule. The Bio-Layer Interferometer can be configured to have substrate immobilized to the sensor surface to measure enzymes whose activity creates a change in the substrate molecular weight, either increasing or diminishing the molecular weight, to produce a corresponding change in the optical layer thickness.

The invention is broadly applicable to enzyme activity measurements, including by way of example but not limitation, measurements of hydrolases (including proteases), glycosylases, esterases, transferases (including nucleotide transferases and phosphotransferases). These are considered in greater detail below.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. Unless otherwise specified, procedures are carried out at room temperature (typically 20-23 degrees Celsius).

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

Example 1

BLI Molecular Weight Detection Characterization

Figure 2:
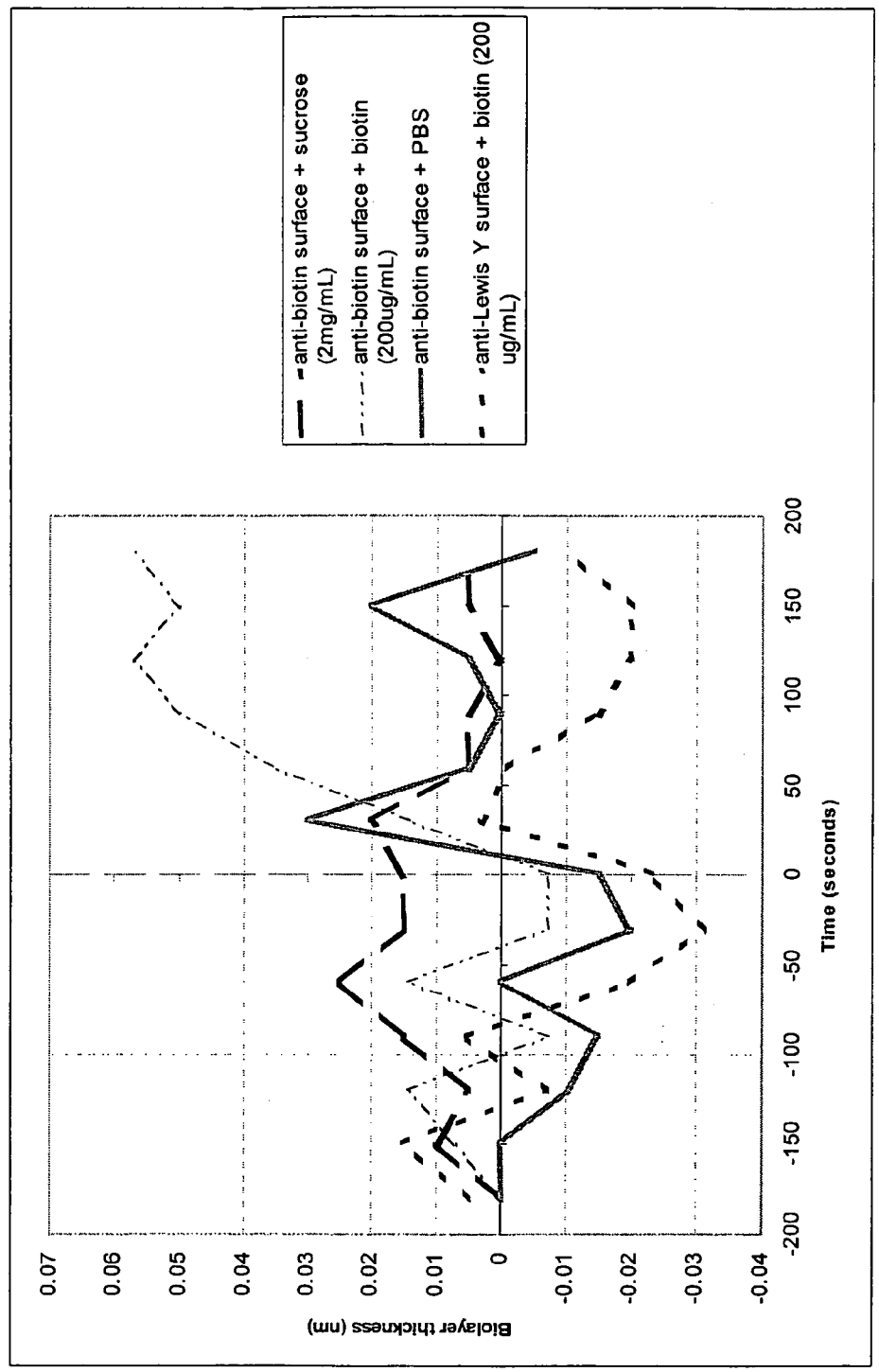
FIG. 2 is another graph illustrating minimum molecular size detection.

The minimum molecular weight of a binding molecule that BLI can detect is illustrated in FIGS. 1 & 2. In FIG. 1 data of a biotin-PEG conjugate with a molecular weight of 900 Daltons binding to a streptavidin coated BLI sensor is depicted. The BLI sensor and methods for coating the sensor are described in detail in co-owned U.S. Non-provisional application Ser. No. 10/981,901, filed Nov. 4, 2004, for Hong Tan, et al., entitled "Fiber-Optic Assay Apparatus Based on Phase-Shift Interferometry," FIG. 2 shows the binding of biotin (M.W. ~230 D) to a streptavidin coated BLI sensor. The data indicate that the described interferometry methods readily detect binding of molecules around 250 Dalton molecular weight, and that molecules in the 500 to 1000 Dalton molecular weight range generate a substantial change in optical layer thickness. Based on the minimum molecular size detection of BLI, one can configure the BLI sensor with immobilized substrates to monitor the activity of enzymes producing molecular size changes in the substrate as small as 250 to 1000 Daltons.

The small minimum molecular size detection limit of BLI makes it possible to apply BLI to a large number of enzymes. The following are by way of example, but not limitation, enzyme classes whose activities can be measured in accordance with the present invention, and specific examples of such measurements.

Example 2

Hydrolase Activity Measurements

Hydrolyases are enzymes that catalyze cleavage of C—O, C—N, C—C or phosphoric anhydride bonds.

Subgroup 1: Proteases (Enzymes Acting on Peptide Bonds)
Immobilized Substrate Format This format features the protease substrate immobilized to the surface of the BLI glass fiber sensor using methods described in co-owned U.S. Non-provisional application Ser. No. 10/981,901, filed Nov. 4, 2004, for Hong Tan, et al., entitled "Fiber-Optic Assay Apparatus Based on Phase-Shift Interferometry," (incorporated herein by reference) and below. The fiber is immersed in an enzyme-containing sample, and monitored for changes in optical layer thickness.

The basic assay protocol is to incubate a Bio-Layer Interferometer (BLI) sensor on which has been immobilized an enzyme substrate in an enzyme-containing solution enzyme. The amount of the substrate depletion is quantified by, e.g., a change in optical phase shift using the Bio-Layer Interferometry (BLI) technique fully described in co-owned and pending U.S. Non-provisional application Ser. No. 10/981,901, filed Nov. 4, 2004, for Hong Tan, et al., entitled "Fiber-Optic Assay Apparatus Based on Phase-Shift Interferometry," incorporated herein by reference. The change in, e.g., optical phase shift is proportional to the amount of enzyme activity in the solution because hydrolytic activity is estimated by measuring the depletion of substrate from the BLI sensor resulting from the enzyme activity.

Subtilisin Activity Measurements on Immobilized Casein Substrate
Methods

An optical signal baseline was established by immersing the optically-activated end of a fiber sensor tip in PBS and monitoring the optical signal using interferometry methods and instrumentation described in co-owned U.S. Non-provisional application Ser. No. 10/981,901, filed Nov. 4, 2004, for Hong Tan, et al, entitled "Fiber-Optic Assay Apparatus Based on Phase-Shift Interferometry," (incorporated herein by reference in its entirety). Next the fiber was coated with Poly-D-Lysine by incubating the tip in a 0.5 mg/mL Poly-D-Lysine solution (in PBS, pH 7.4) for 15 minutes. Unbound Poly-D-Lysine was rinsed by incubating the tips in PBS for 10 minutes.

The fiber was coated with a layer of casein [Sigma Chemical Company, St Louis, Mo.] by incubating the tip in a 50 μg/mL casein solution (50 mM Na Phosphate, 150 mM NaCl, pH 7) for 15 minutes. Unbound casein was rinsed by incubating the tip in PBS for 10 minutes.

Fibers with immobilized casein were incubated in various concentrations (1, 10, 50 μg/mL) of subtilisin [Sigma Chemical Company, St Louis, Mo.] solution (in 50 mM Na Phosphate, 150 mM NaCl, pH 7). Each of the procedures described above was carried out while monitoring the optical signal.

Results and Discussion

Figure 3:
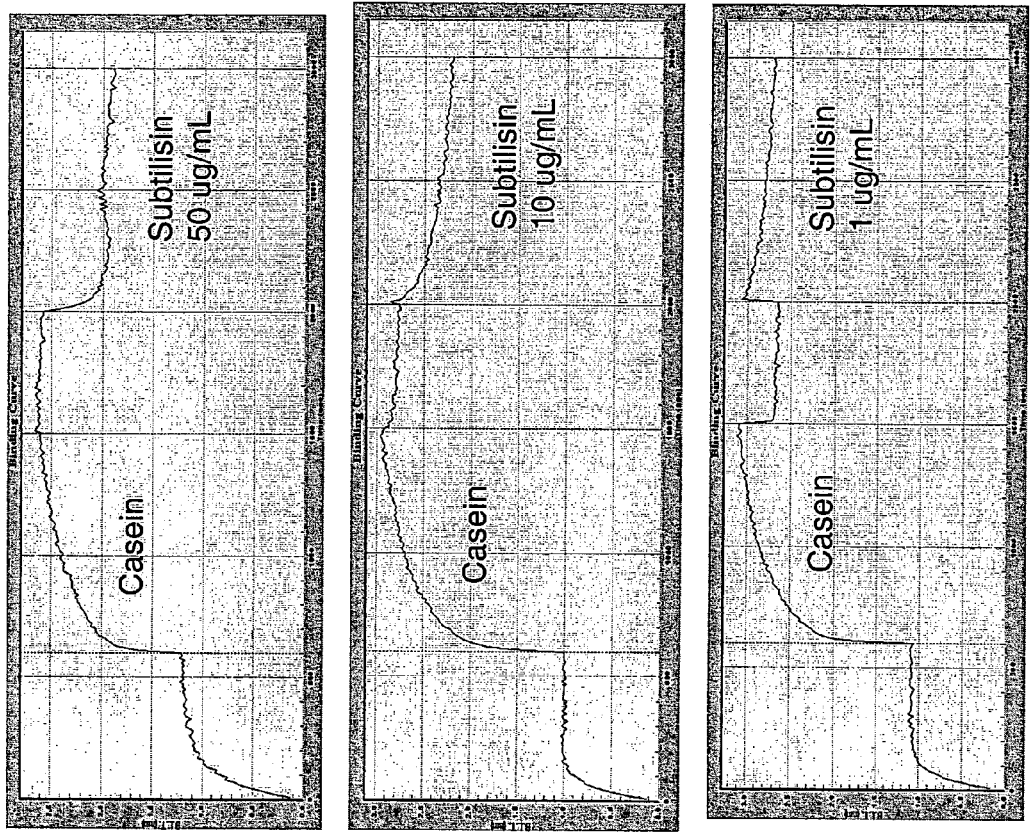
FIG. 3 is a graph illustrating subtilisin activity measurement at three enzyme concentrations.

FIG. 3 illustrates the result of this example. The optical traces show calculated illustrate biolayer thickness as a function of time. Apparent are increases in biolayer thickness during casein loading and subsequent decreases following subtilisin incubation. The traces show a clear dose-response effect with more rapid and greater changes occurring with higher subtilisin concentration over the tested range.

Effect of Protease Inhibitor on Enzymatic Activity
Methods

Fiber sensor tips were prepared and coated with casein as described above. One fiber was incubated in 50 μg/mL of subtilisin solution (in 50 mM Na Phosphate, 150 mM NaCl, pH 7).

Other fibers were incubated in a pre-mixed and pre-incubated solution of 50 μg/mL of subtilisin and 3 mM PMSF [Sigma Chemical Company, St Louis, Mo.] (the mixture was incubated at 37° C. for 20 minutes) solution (50 mM Na Phosphate, 150 mM NaCl, pH 7). Each of the procedures described above was carried out while monitoring the optical signal.

Result and Discussion

Figure 4:
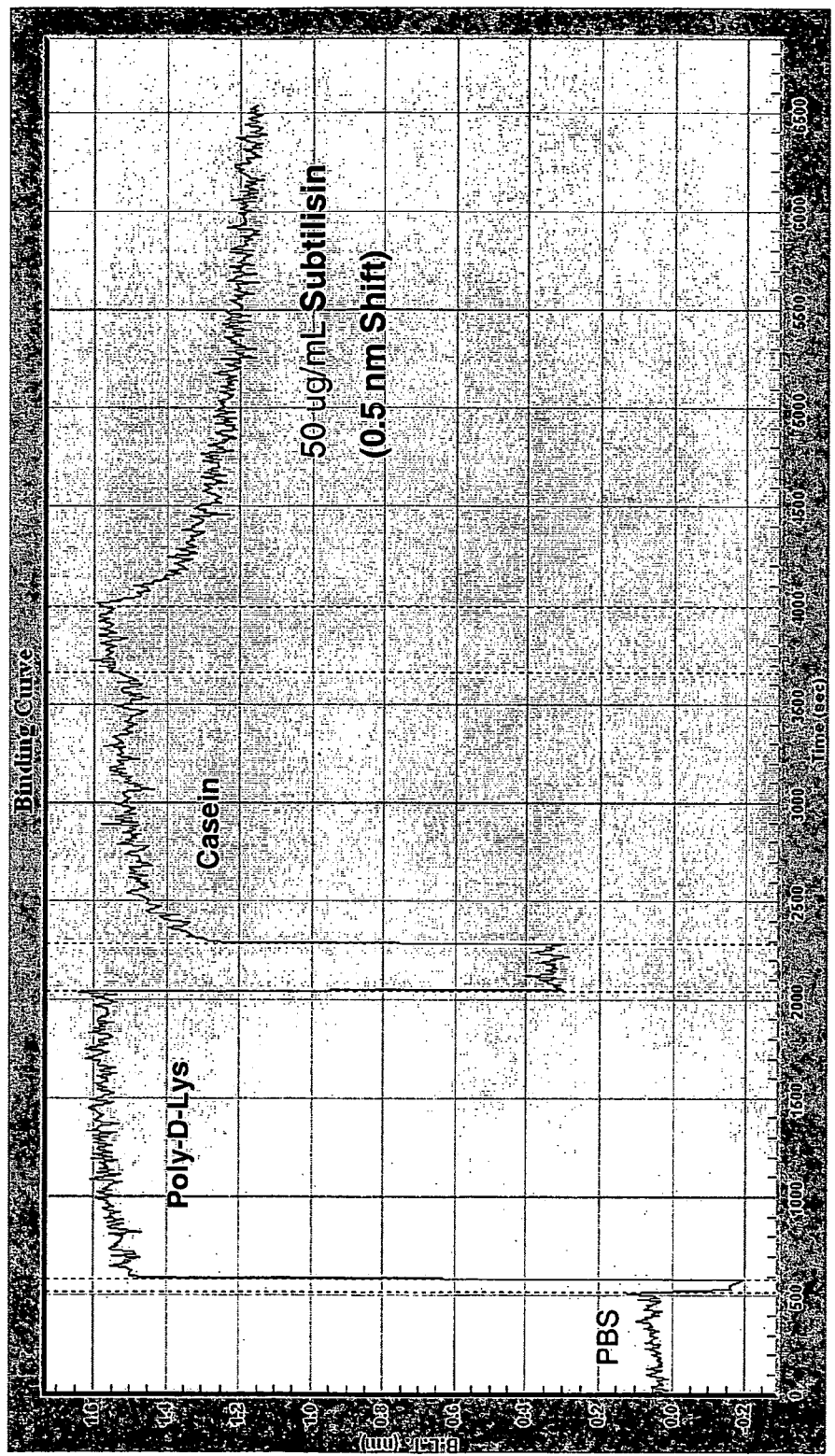
FIG. 4 is a graph illustrating subtilisin activity measurement at 50 µg/ml.
Figure 5:
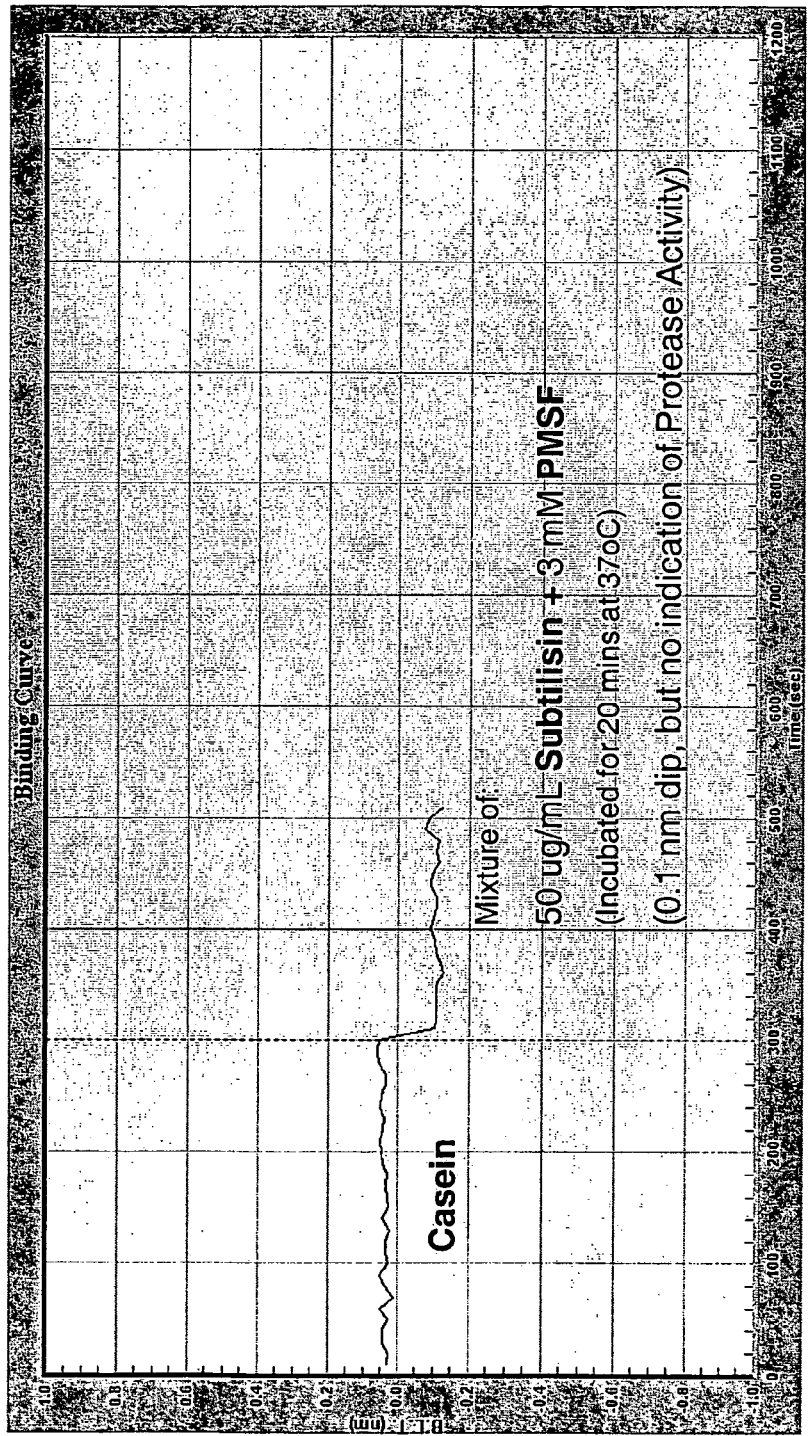
FIG. 5 is a graph illustrating effect of protease inhibitor on subtilisin activity.
Figure 6:
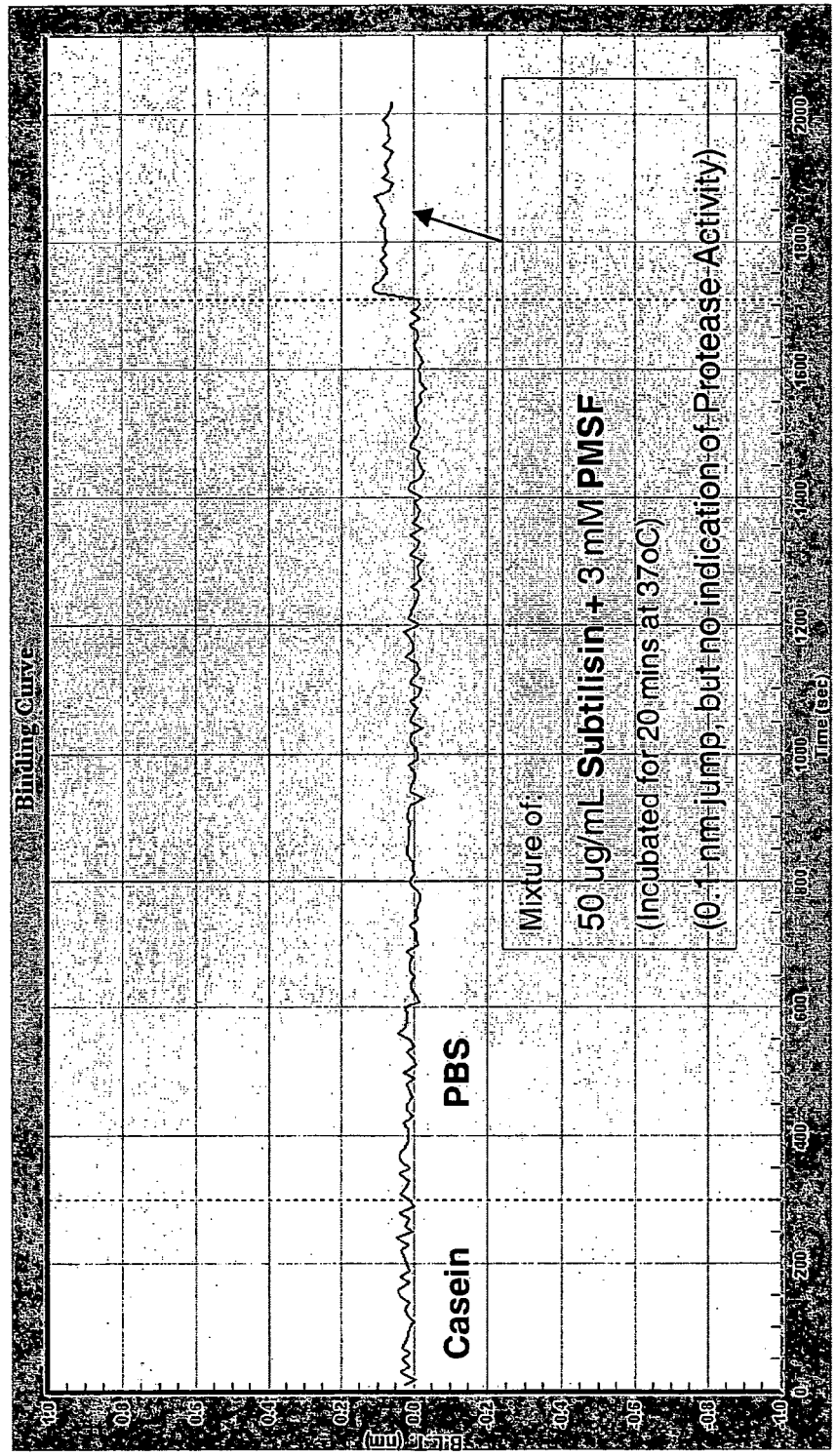
FIG. 6 is a second graph illustrating effect of protease inhibitor on subtilisin activity.

Traces obtained from a fiber incubated in subtilisin solution show the expected depletion of casein from the tip surface (FIG. 4). This shows up as smooth, time-dependent change in the trace following incubation in the enzyme solution. Fibers incubated in the subtilisin/PMSF mixture of subtilisin and (protease inhibitor) PMSF did not show the any time-dependent changes in the optical signal (FIGS. 5 and 6), illustrating inhibition of subtilisin by 3 mM PMSF.

Substrate Capture Format

Figure 7:
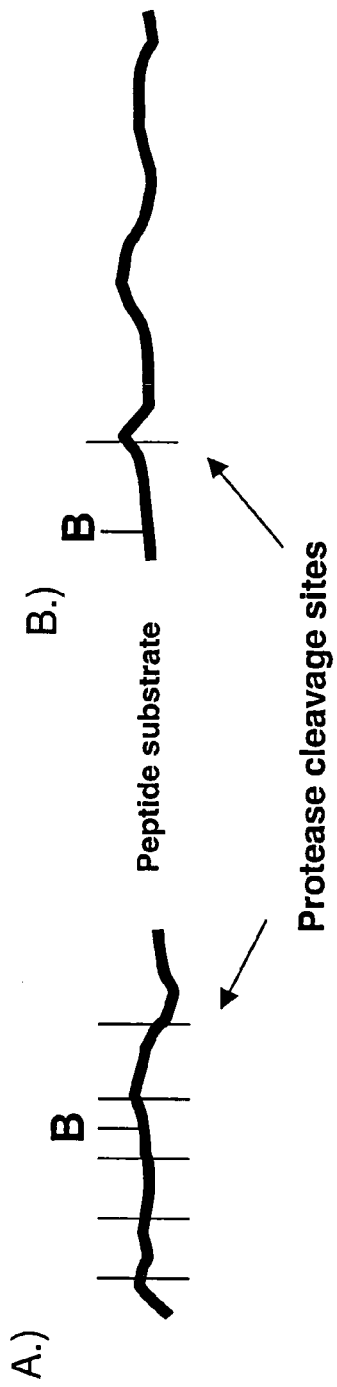
FIG. 7 is a diagram illustrating substrate preparation for substrate capture format.

The substrate capture format entails digestion of the substrate by a protease in liquid phase followed by binding of the substrate to the surface of the BLI sensor. The binding of the substrate is designed so that proteolytic cleavage of the substrate produces a detectable to change in the optical layer thickness. In one preferred embodiment, a streptavidin/biotin binding pair is used to effect substrate capture. FIG. 7 shows two approaches to tag the peptide substrate with biotin. In the case where the protease has multiple cleavage sites, the biotin does not have to be substituted at a specific site since the resulting digestion will produce a peptide with a sufficiently small molecular size. The substrate can also be designed so that there is a single cleavage site and the location of the biotin substitution is such that it remains on the smallest peptide fragment upon proteolysis. Methods for derivatizing substrate with biotin or another member of a binding pair are well known to ordinarily-skilled practitioners and include biochemical modification of existing substrate molecules, or, synthesis using derivatized sub-units. Such methods are described in, e.g., [*Antibodies: A Laboratory Manual* (E. Harlow and D. Lane, 1988); *Bioconjugation Protocols: Strategies and Methods* (Methods in Molecular Biology (Clifton, N.J.), V. 283, 2004)] incorporated by reference, and exemplified below.

Example 3

Trypsin Activity Measurements Using Substrate Capture

Trypsin activity measurements are made using the substrate capture format and cytochrome C as a substrate. Cytochrome C is about 12 kDaltons in molecular weight and includes has 8 trypsin cleavage sites. A standard biotin-NHS derivative [Pierce Biotechnology, Rockford Ill.] is used to tag the cytochrome C. Coupling conditions employ standard phosphate buffered saline (PBS) pH 7 buffer. Biotin-NHS is mixed with cytochrome C at a molar coupling ratio of 5 to 1 (biotin to cytochrome C) typically resulting in one biotin substitution per cytochrome C molecule. Streptavidin-coated BLI sensors are prepared from 0.6 mm diameter glass fibers with a tantalum oxide layer of about 20 nm and a silicon dioxide layer of about 700 nm are dipped in a PBS solution containing 0.5 mg/ml of poly-D-lysine as described above. After 15 minutes at room temperature, the fibers are washed in PBS then immersed in a 1 mg/ml solution of bovine serum albumin (BSA) labeled with N-succinimidiyl 3-(2-pyridyldithio) propionate (SPDP) [Pierce Biotechnology, Rockford Ill.] and incubated for 20 minutes followed by a wash step with PBS. The fibers are then immersed in a solution of 50 mM dithiolthreitol for 30 minutes at room temperature. After a wash in PBS, the fibers are placed in the solution containing 20 μg/ml of streptavidin labeled with SMCC and incubated for 60 minutes, followed a by PBS wash. The fibers are stored in PBS until use.

Figure 8:
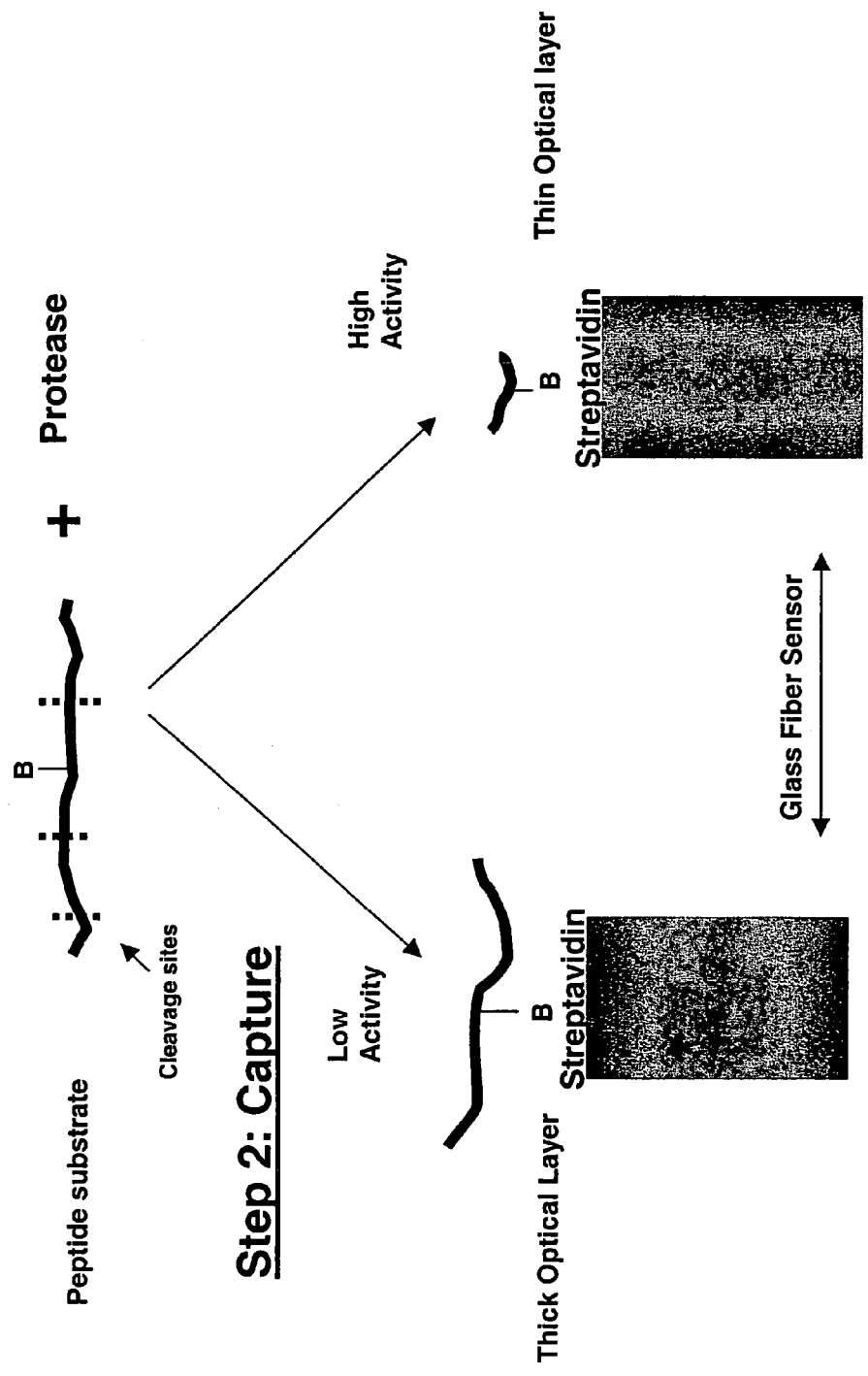
FIG. 8 is a schematic illustrating principle of substrate capture format assays.

The basic assay for protease activity using the substrate capture format entails adding to a biotinylated cytochrome C solution, in the range of about 1 μg/ml to 1 mg/ml, a trypsin sample, typically at a 1% wt./wt. ratio. After a digestion time period, a streptavidin coated sensor is placed in the enzyme/substrate mixture for substrate capture. To avoid trypsin acting upon the streptavidin, the enzyme can be inactivated either by snap boiling the substrate mixture or adding a protease inhibitor, such as aprotinin, just prior to adding the glass fiber. The BLI sensor can assess the change in substrate size by a measuring the optical layer thickness upon binding the biotinylated peptide. FIG. 8 illustrates the assay format where protease activity produces smaller peptides with a thinner optical layer.

Subgroup 2: Glycosylases (Enzymes that Hydrolyse O or S or N Glycosyl Bonds) Immobilized Substrate Format The following example is described for dextranase, but the same methods can be applied to other polysaccharide processing enzymes such as amylase and cellulase. Dextran is linked to a protein coated BLI sensor by initially reacting the dextran with sodium periodate to introduce reactive aldehyde groups on the dextran polymer. A protein coated BLI sensor (such as prepared according to the methods described in the example above) is then immersed in the dextran solution. The aldehyde groups on the dextran form bonds with free amino groups on the protein resulting in a BLI sensor with a dextran as the final layer. Measurement of dextranase activity is possible when the dextran coated sensor is immersed in a dextranase containing sample. Hydrolytic activity of the dextranase reduces the molecular size of the immobilized dextran, which is detected as a thinner optical layer.

Substrate Capture Format

Measurement of glycosylases in the substrate capture format is accomplished by biotinylating the polysaccharide substrate. In the dextranase example, dextran is reacted with sodium periodate to generate aldehyde groups followed by the addition of large molar excess of a bis-amine, such as ethylenediamine. One amino group of the bis-amine couples to the aldehyde on the dextran leaving the second amine free for coupling to biotin-NHS in a subsequent reaction. The molar coupling ratio of the biotin-NHS reaction is selected to yield about one biotin substitution per dextran. The assay for dextranase activity in the substrate capture format is similar to the protease second example where the biotinylated dextran substrate is incubated with the dextranase sample followed by binding of the biotinylated dextran to a streptavidin coated BLI sensor. Dextranase activity creates smaller dextran fragments which are measured as a thinner optical layer.

Example 4

Esterase Activity Measurements

Subgroup 3: Esterases (Enzymes that Act on Ester Bonds)

Some examples of esterases include nucleases (RNase, DNase, etc.), alkaline phosphatase, acid phosphatase, and serine/threonine phosphatase. DNase I is used as an example of measuring esterase activity. Since DNase I cleaves at all 4 bases in oligonucleotides as small as three bases in length, dsDNA is prepared by a commercial vendor using standard DNA synthesis techniques having a length of about 30-40 base pairs with a biotin group at one of the terminal ends. The biotinylated dsDNA is bound to a streptavidin coated BLI sensor. The sensor is then immersed in sample containing DNase I in the buffer: 10 mM Tris pH 7.5, 2.5 $MgCl_2$, 0.5 nM $CaCl_2$ and the decrease in optical layer thickness is monitored. The alternative substrate capture format is performed by mixing the biotin labeled dsDNA with the DNase I in liquid phase before the binding of the substrate to the streptavidin coated sensor.

Example 5

Transferase Activity Measurements

Transferases are enzymes that catalyze the transfer of methyl, glycosyl, or phospho groups to other compounds. In contrast to the hydrolytic enzymes, the transferases increase the molecular size of the substrate and their activity is detected by the BLI sensor as an increase in optical layer thickness.

Subgroup 1: Nucleotide Transferases

Figure 9:
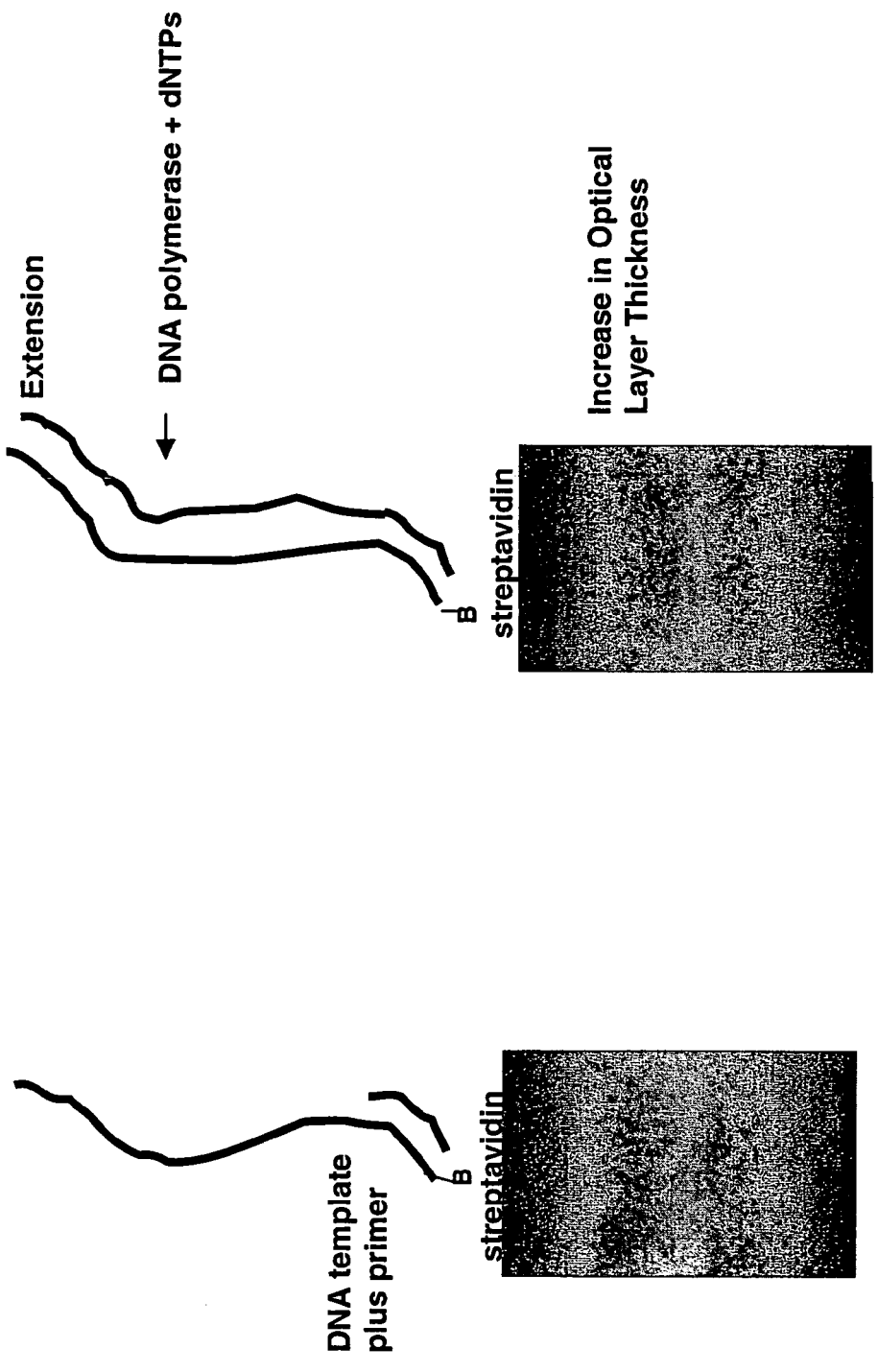
FIG. 9 is a schematic illustrating method to detect nucleotide transferase activity.

Nucleotides transferases catalyze the incorporation of nucleotides into DNA or RNA polymers. FIG. 9 shows the format for measuring DNA polymerase I activity as an example. A DNA template from 10 to 30 nucleotides is obtained from a commercial vendor with a biotin incorporation at either of the terminal nucleotides. The DNA template is hybridized with an oligonucleotide primer enabling the DNA polymerase I to incorporate nucleotides in the 5' to 3' direction. The biotin tagged DNA template can be bound to a streptavidin coated sensor either before or after the DNA polymerase step. Conditions for the polymerase step such as enzyme loading, dNTPs, buffer formulation, etc. follow established protocols. Since the dNTPs have molecular weights around 400 D, incorporation of as little as 1-2 nucleotides can be detected as a change in optical thickness.

Figure 10:
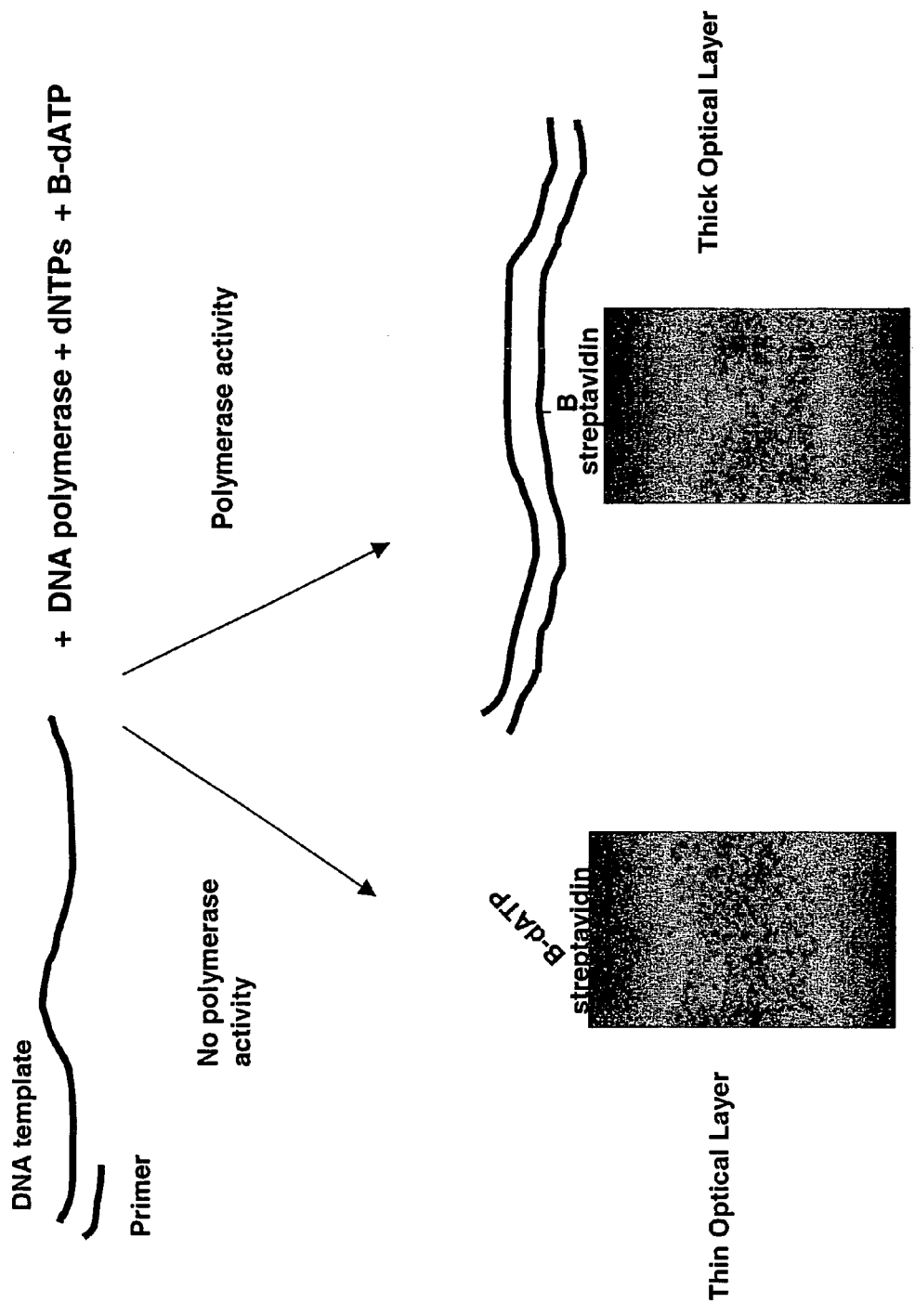
FIG. 10 is a schematic illustrating method to detect nucleotide transferase activity with hapten incorporation.

An alternative approach to measure activity of nucleotide transferases is based on hapten incorporation as shown in FIG. 10. A DNA template with a hybridized primer as mixed with DNA polymerase I and a mixture of dNTPs including biotinylated ATP. B-ATP is obtained from commercial sources since it is commonly used in nick translation. After the polymerase step, a streptavidin coated BLI sensor is placed in the sample mixture. Unincorporated B-ATP having a molecular weight around 600 D produces a relatively small increase in the optical layer upon binding to streptavidin, whereas B-ATP incorporated in the DNA template produces a greater increase in the optical layer depending on the molecular weight of the DNA.

Subgroup 2: Phosphotransferases

Figure 11:
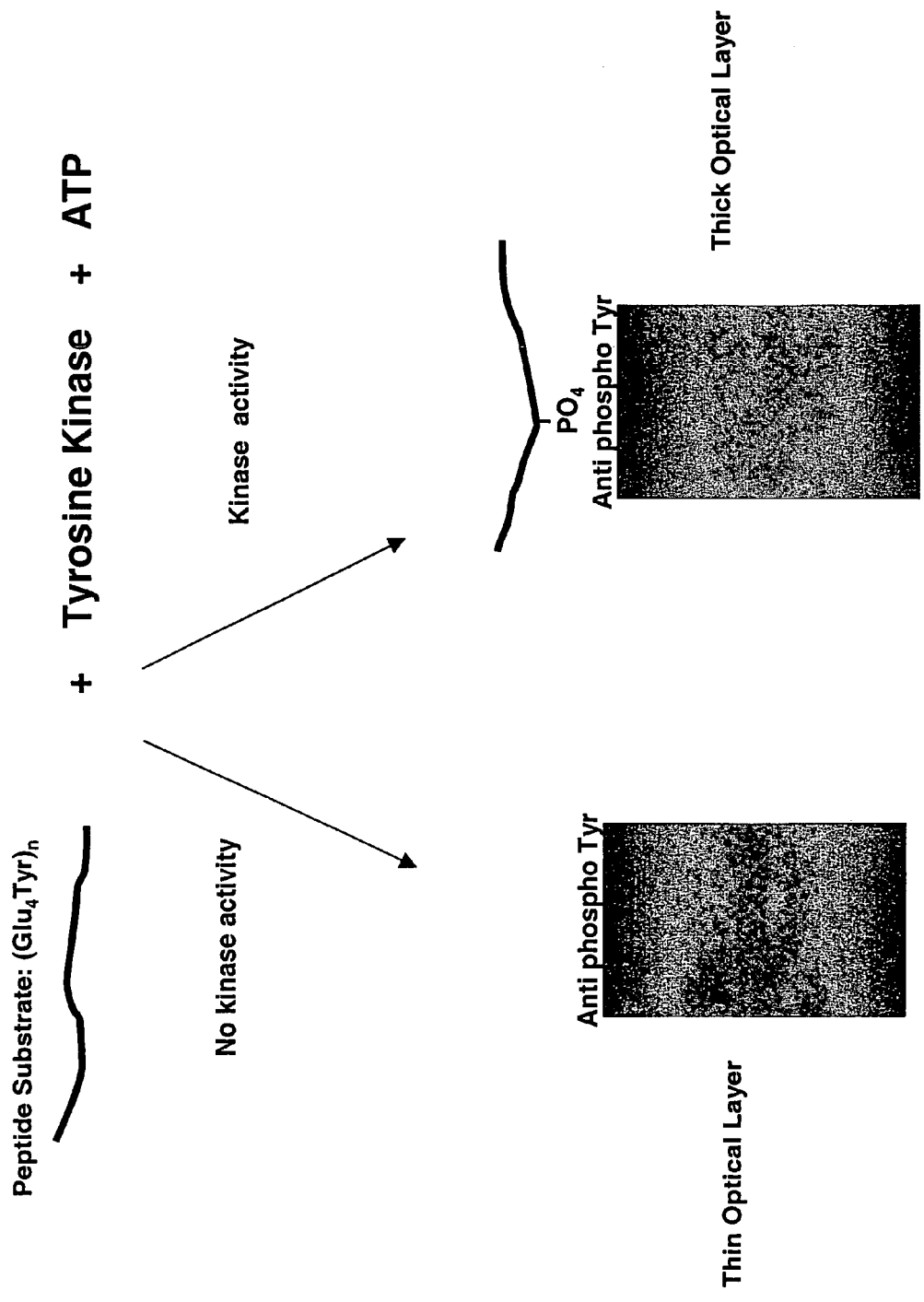
FIG. 11 is a schematic illustrating method to detect phosphotransferase activity using antibody to phosphorylated substrate.

Phosphotransferases catalyze the transfer of phosphate groups to hydroxyl containing compounds, typically peptides with tyrosine, serine, or threonine residues. There are over 100 commercially monoclonal antibodies that bind to a phosphorylated amino acid or specific sequences encompassing a phosphorlyated amino acid. Many assays of kinase activity have been reported and are commercially available utilizing antibodies to phosphorylated peptide substrates. FIG. 11 describes an assay using an anti phosphotyrosine antibody. The antibody is initially biotinylated by standard methods then bound to a streptavidin coated sensor. The substrate $(Glu_4Tyr)_n$ is incubated with tyrosine kinase plus ATP, after which the sensor coated with anti phosphotyrosine is placed in the sample. The binding of the phosphorylated peptide produces an increase in the optical layer thickness.

Figure 12:
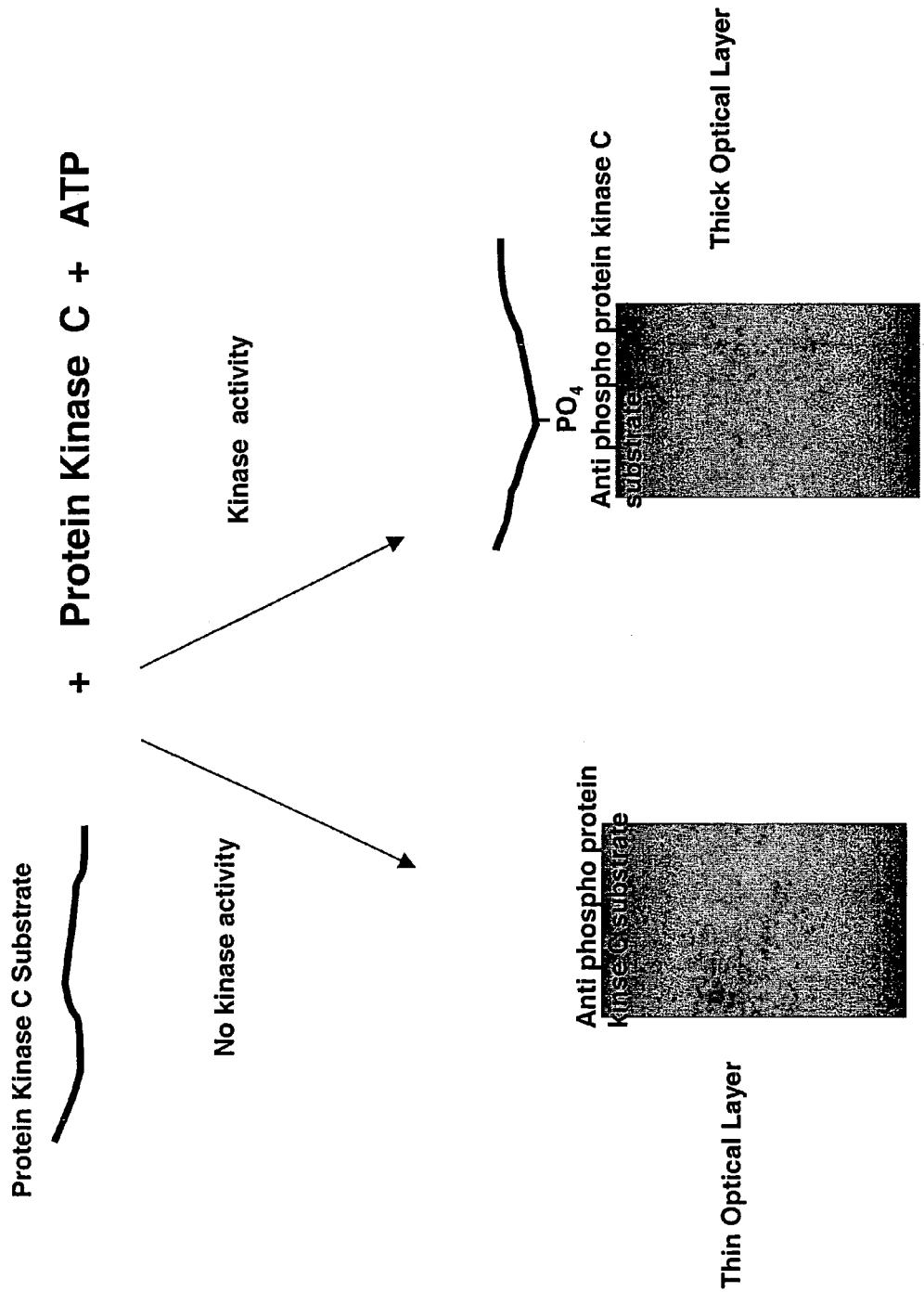
FIG. 12 is a schematic illustrating method to detect protein kinase C activity.

FIG. 12 illustrates an assay using an antibody to a phosphorylated amino acid sequence for a specific kinase. In this case, the kinase is protein kinase C and commercial antibody to phosphorylated protein kinase C substrate. FIG. 13 shows an exemplary format for a kinase activation assay. In this example, mitogen activated protein kinase (MAPK) is activated by phosphorylation by another enzyme, MEK1. A commercial anti phospho MAPK bound to a BLI sensor detects the activation of MAPK.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method for assaying enzyme activity, comprising:
   providing an optical element coupled to a light source via a mechanical coupling that engages the optical element with an optical fiber and provides an air gap between the optical element and the fiber, the optical element including (a) a proximal reflecting surface and a distal reflecting surface separated by at least 50 nm, and (b) a layer of enzyme substrate molecules positioned so that interference between a reflected beam from the proximal reflecting surface and a reflected beam from the distal reflecting surface varies as an enzyme reacts with the substrate, and wherein the reflected beams are coupled into the optical fiber;
   exposing the optical element to an enzyme; and
   detecting a change in the interference between the reflected beams, wherein the change is indicative of enzyme activity.

2. The method of claim 1, wherein the enzyme is a hydrolase or a transferase.

3. The method of claim 2, wherein the enzyme is a protease, a phosphatase, a glycosylase, or an esterase.

4. The method of claim 2, wherein the enzyme is a nucleotide transferase, a glycosyl transferase or a phosphotransferase.

5. The method of claim 1, further comprising providing a second optical element coupled to the light source via a second fiber, the second optical element including (c) a proximal reflecting surface and a distal reflecting surface separated by at least 50 nm, and (d) a layer of enzyme binding molecules positioned so that interference between a second reflected beam from the second optical element proximal reflecting surface and a reflected beam from the second optical element distal reflecting surface varies as the enzyme binds to the layer of enzyme binding molecules, and wherein the second reflected beams are coupled into the fiber; and detecting a change in the interference between the second reflected beams, wherein the change is indicative of enzyme activity.

6. The method of claim 5, wherein the layer of enzyme binding molecules comprises an anti-enzyme antibody, a fragment of an anti-enzyme antibody, or an anti-enzyme scFv molecule.

7. The method of claim 1, wherein the optical element is a first optical element, and wherein the method further comprises providing a second optical element positioned between the proximal reflecting surface of the first optical element and the fiber, the second optical element being coupled to the light source via the mechanical coupling that engages the second optical element with the fiber and provides an air gap between the second optical element and the fiber, and wherein the first optical element is coupled to the second optical element at the proximal reflective surface.

8. A method for assaying enzyme activity, comprising:
   providing an optical element coupled to a light source via a mechanical coupling that engages the first optical element with a fiber and provides an air gap between the first optical element and the fiber, the optical element including (a) a proximal reflecting surface and a distal reflecting surface separated by at least 50 nm, and (b) a layer of analyte binding molecules;
   exposing the optical element to an enzyme substrate reacted or reacting with an enzyme, whereby the enzyme substrate or a portion of the enzyme substrate binds to the layer of analyte binding molecules, and wherein interference between a reflected beam from the proximal reflecting surface and a reflected beam from the distal reflecting surface varies as the enzyme substrate or portion thereof binds to the layer of enzyme binding molecules, the reflected beams coupled into the fiber; and
   detecting a change in optical thickness of the first reflecting surface, wherein the change is indicative of enzyme activity.

9. The method of claim 8, wherein the enzyme is a hydrolase or a transferase.

10. The method of claim 9, wherein the enzyme is a protease, a phosphatase, a glycosylase, or an esterase.

11. The method of claim 9, wherein the enzyme is a nucleotide transferase, a glycosyl transferase or a phosphotransferase.

12. The method of claim 8, further comprising interposing a semi-permeable membrane between said optical element and said substrate.

13. The method of claim 8, wherein said substrate is bound to a support.

14. The method of claim 8, further comprising providing a second optical element coupled to the light source via a second fiber, the second optical element including (c) a proximal reflecting surface and a distal reflecting surface separated by at least 50 nm, and (d) a layer of enzyme binding molecules positioned so that interference between a second reflected beam from the second optical element proximal reflecting surface and a reflected beam from the second optical element distal reflecting surface varies as the enzyme binds to the layer of enzyme binding molecules, and wherein the second reflected beams are coupled into the fiber; and detecting a change in the interference between the second reflected beams, wherein the change is indicative of enzyme activity.

15. The method of claim 14, wherein the layer of enzyme binding molecules comprises an anti-enzyme antibody, a fragment of an anti-enzyme antibody, or an anti-enzyme scFv molecule.

16. The method of claim 8, wherein the layer of analyte binding molecules comprises avidin, streptavidin, biotin, an antibody, an antibody fragment, an scFv, or a lectin.

17. The method of claim 8, further comprising the step of inactivating the enzyme before the exposing step.

18. The method of claim 8, wherein the optical element is a first optical element, and wherein the method further comprises providing a second optical element positioned between the proximal reflecting surface of the first optical element and the fiber, the second optical element being coupled to the light source via the mechanical coupling that engages the second optical element with the fiber and provides an air gap between the second optical element and the fiber, and wherein the first optical element is coupled to the second optical element at the proximal reflective surface.

* * * * *